(12) United States Patent
Tois et al.

(10) Patent No.: US 9,321,712 B2
(45) Date of Patent: Apr. 26, 2016

(54) PROCESS FOR THE PREPARATION OF OSPEMIFENE

(71) Applicant: Fermion Oy, Espoo (FI)

(72) Inventors: Jan Tois, Espoo (FI); Ainoliisa Pihko, Espoo (FI); Arne Grumann, Kauniainen (FI)

(73) Assignee: FERMION OY, Espoo (FI)

( * ) Notice: Subject to any disclaimer, the term of this patent is extended or adjusted under 35 U.S.C. 154(b) by 0 days.

(21) Appl. No.: 14/436,706

(22) PCT Filed: Oct. 17, 2013

(86) PCT No.: PCT/FI2013/000039
§ 371 (c)(1),
(2) Date: Apr. 17, 2015

(87) PCT Pub. No.: WO2014/060639
PCT Pub. Date: Apr. 24, 2014

(65) Prior Publication Data
US 2015/0274624 A1  Oct. 1, 2015

Related U.S. Application Data

(60) Provisional application No. 61/716,171, filed on Oct. 19, 2012.

(51) Int. Cl.
| | | |
|---|---|---|
| *C07C 41/26* | (2006.01) | |
| *C07C 69/24* | (2006.01) | |
| *C07C 67/14* | (2006.01) | |
| *C07C 67/293* | (2006.01) | |
| *C07C 67/297* | (2006.01) | |
| *C07C 69/28* | (2006.01) | |
| *C07C 69/753* | (2006.01) | |
| *C07C 69/76* | (2006.01) | |

(52) U.S. Cl.
CPC .......... *C07C 41/26* (2013.01); *C07C 67/14* (2013.01); *C07C 67/293* (2013.01); *C07C 67/297* (2013.01); *C07C 69/24* (2013.01); *C07C 69/28* (2013.01); *C07C 69/753* (2013.01); *C07C 69/76* (2013.01); *C07C 2101/02* (2013.01); *C07C 2103/74* (2013.01)

(58) Field of Classification Search
CPC .................................................. C07C 41/26
See application file for complete search history.

(56) References Cited

U.S. PATENT DOCUMENTS

| | | |
|---|---|---|
| 2,182,786 A | 12/1939 | Coleman et al. |
| 2,831,768 A | 4/1958 | Merrill et al. |
| 4,117,121 A | 9/1978 | Gallo-Torres |
| 4,625,048 A | 11/1986 | Zurfluh |
| 4,656,187 A | 4/1987 | Black et al. |
| 4,696,949 A | 9/1987 | Toivola et al. |
| 4,894,373 A | 1/1990 | Young |
| 4,935,243 A | 6/1990 | Borkan et al. |
| 4,996,225 A | 2/1991 | Toivola et al. |
| 5,118,667 A | 6/1992 | Adams et al. |
| 5,118,859 A | 6/1992 | Aumueller et al. |
| 5,189,212 A | 2/1993 | Ruenitz |
| 5,192,525 A | 3/1993 | Yang et al. |
| 5,196,435 A | 3/1993 | Clemens et al. |
| 5,352,699 A | 10/1994 | Jackson |
| 5,446,203 A | 8/1995 | McNelis |
| 5,470,883 A | 11/1995 | Stromberg |
| 5,491,173 A | 2/1996 | Toivola et al. |
| 5,567,714 A | 10/1996 | Bruns |
| 5,658,931 A | 8/1997 | Bryant et al. |
| 5,691,355 A | 11/1997 | Bryant et al. |
| 5,693,674 A | 12/1997 | Bitoniti |
| 5,719,136 A | 2/1998 | Chwalisz et al. |
| 5,747,059 A | 5/1998 | Korsgaard et al. |

(Continued)

FOREIGN PATENT DOCUMENTS

| | | |
|---|---|---|
| CS | 196471 | 3/1980 |
| EP | 0072475 | 2/1983 |

(Continued)

OTHER PUBLICATIONS

International Search Report issued Feb. 10, 2014 in PCT/FI2013/000039.
Dan Zhang, et al., "Two-step synthesis technology of ospemifene", Drugs & Clinic, vol. 27, No. 4, Mar. 29, 2012, XP002719433, pp. 351-352 (with English abstract).
C.A. Zhang, et al., "Results Summary", May 29, 2015, p. 1-3.
U.S. Appl. No. 14/436,690, filed Apr. 17, 2015, Tois, et al.
Ferguson et al., Alkali Metal Ion Mediated Cyclization of 4,4'-(3,6-dioxaocta-1,8-diyloxy}-bis(benzophenone), Tetrahedron Letters, Jun. 1993, vol. 34, No. 23, pp. 3719-3722.

(Continued)

*Primary Examiner* — Yong Chu
*Assistant Examiner* — Ana Z Muresan
(74) *Attorney, Agent, or Firm* — Oblon, McClelland, Maier & Neustadt, L.L.P.

(57) ABSTRACT

The present invention is related to the process for the preparation ospemifene or (Z)-2-[4-(4-chloro-1,2-diphenyl-but-1-enyl)phenoxy]ethanol (I) and to intermediate compounds used in the process.

(I)

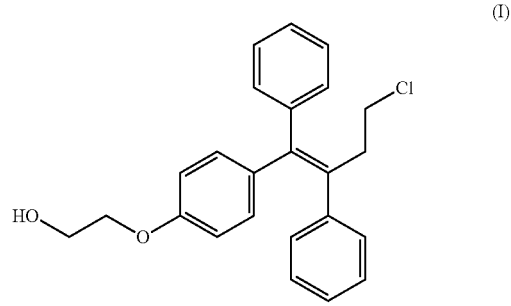

30 Claims, No Drawings

(56) References Cited

U.S. PATENT DOCUMENTS

| | | | |
|---|---|---|---|
| 5,750,576 | A | 5/1998 | DeGregorio et al. |
| 5,807,899 | A | 9/1998 | Bohlmann et al. |
| 5,821,254 | A | 10/1998 | Sporn et al. |
| 5,827,892 | A | 10/1998 | Loser et al. |
| 5,852,059 | A | 12/1998 | Thompson |
| 5,877,219 | A | 3/1999 | Willson |
| 5,912,273 | A | 6/1999 | Degregorio et al. |
| 6,037,379 | A | 3/2000 | Harkonen et al. |
| 6,245,342 | B1 | 6/2001 | Golz-Berner et al. |
| 6,245,352 | B1 | 6/2001 | Arbuthnot et al. |
| 6,245,819 | B1 | 6/2001 | Halonen et al. |
| 6,525,084 | B2 | 2/2003 | Rasmussen et al. |
| 6,576,645 | B1 | 6/2003 | Sodervall et al. |
| 6,632,447 | B1 | 10/2003 | Steiner et al. |
| 6,875,775 | B2 | 4/2005 | Sodervall et al. |
| 6,984,665 | B2 | 1/2006 | Blom et al. |
| 7,504,530 | B2 | 3/2009 | Sodervall et al. |
| 2001/0034340 | A1 | 10/2001 | Pickar |
| 2004/0248989 | A1 | 12/2004 | Santti et al. |
| 2005/0182143 | A1 | 8/2005 | Anttila |
| 2005/0187302 | A1 | 8/2005 | Blom |
| 2005/0215528 | A1 | 9/2005 | Furuya et al. |
| 2007/0104742 | A1 | 5/2007 | Lehtola et al. |
| 2007/0197664 | A1 | 8/2007 | Steiner et al. |
| 2007/0203180 | A1 | 8/2007 | Hoekstra et al. |
| 2008/0207956 | A1 | 8/2008 | Sodervall et al. |
| 2008/0214860 | A1 | 9/2008 | Sodervall et al. |

FOREIGN PATENT DOCUMENTS

| | | |
|---|---|---|
| EP | 0 095 875 A3 | 12/1983 |
| EP | 0425974 | 5/1991 |
| EP | 0 664 124 A1 | 7/1995 |
| EP | 0 779 808 B1 | 8/1999 |
| EP | 0 760 651 B1 | 7/2001 |
| EP | 1 125 582 A2 | 8/2001 |
| WO | WO92/06068 A1 | 4/1992 |
| WO | WO 93/19746 A1 | 10/1993 |
| WO | WO 95/26720 A1 | 10/1995 |
| WO | WO 96/07402 A1 | 3/1996 |
| WO | WO 96/35417 A1 | 11/1996 |
| WO | WO 96/40616 A1 | 12/1996 |
| WO | WO 97/32574 A1 | 9/1997 |
| WO | 9942427 | 8/1999 |
| WO | WO 99/42427 A1 | 8/1999 |
| WO | WO 99/63974 A2 | 12/1999 |
| WO | WO 01/36360 A1 | 5/2001 |
| WO | 0160775 | 8/2001 |
| WO | WO 01/54699 A1 | 8/2001 |
| WO | WO 02/07718 A1 | 1/2002 |
| WO | WO 02/090305 A1 | 11/2002 |
| WO | WO 03/047504 A2 | 6/2003 |
| WO | WO 03/103649 A1 | 12/2003 |
| WO | WO 2005/079777 A1 | 9/2005 |

OTHER PUBLICATIONS

Jordan, V. Craig; "Antiestrogens and Selective Estrogen Receptor Modulators as Multifunctional Medicines, 2. Clinical Considerations and New Agents," Journal of Medicinal Chemistry, vol. 46, No. 7, Mar. 27, 2003, pp. 1081-1111.

Kangas, L., "Biochemical and pharmacological effects toremifene metabolities," Cancer Chemother. Pharmacol. 27:8-12, Springer-Verlag (Apr. 1990).

S.K. Voipio, et al., "Effects of ospemifene (FC-1271 a) on uterine endometrium, vaginal maturation index, and honnonal status in healthy postmenopausal women." Maturitas vol. 43, 207-214 (2002).

Qu, Q. et al., "Selective Estrogenic Effects of a Novel Triphenylethylene Compounds, FC1271a, on Bone, Cholesterol Level, and Reproductive Tissues in Intact and Ovariectomized Rats," Endocrinology 141: 809-820, Association for the Study of Internal Secretions (Feb. 2000).

Salvolainen-Peltonen et al.; "Selective Estrogen Receptor Modulators Prevent Neointima Fonnation After Vascular Injury"; Molecular and Cellular Endocrinology, vol. 227, 2004, pp. 9-20.

Duan et al., "Insights into the General and Efficient Cross McMurry Reactions between Ketones," J. Org. Chem. 2006, 71, 9873-9876.

International Search Report and Written Opinion for PCT/GB2011/000058 dated Apr. 21,2011.

International Search Report for PCT/FI2008/050057 dated Apr. 18, 2008.

PROCESS FOR THE PREPARATION OF OSPEMIFENE

CROSS REFERENCE TO RELATED APPLICATION

This application is a National Stage entry under 35 USC 371 of PCT/FI2013/000039, filed on Oct. 17, 2013, which is a nonprovisional application of U.S. Provisional Patent Application No. 61/716,171, filed on Oct. 19, 2012.

FIELD OF THE INVENTION

The invention is related to a process for the preparation ospemifene and to intermediate compounds used in the process.

BACKGROUND OF THE INVENTION

Ospemifene or (Z)-2-[4-(4-chloro-1,2-diphenyl-but-1-enyl)phenoxy]ethanol is represented by formula (I):

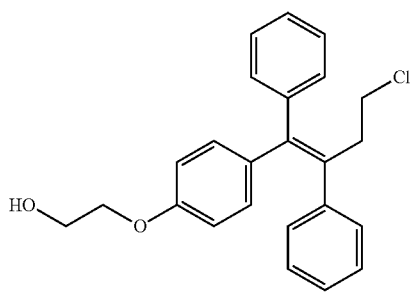

(I)

Ospemifene is an estrogen receptor agonist/antagonist currently investigated e.g. for the treatment of vulvar and vaginal atrophy due to menopause.

Preparation of ospemifene starting from Z-4-(4-hydroxy-1,2-diphenyl-but-1-enyl)phenol has been described in WO 96/07402. Use of McMurry coupling reaction for the manufacture of ospemifene has been described in WO 2008/099059 and WO 2011/089385. These methods suffer from the drawback that large amounts of expensive reagents or solvents, such as titanium tetrachloride, $LiAlH_4$, and 2-Me-THF, are needed:

Thus, it is desirable to provide an improved method for producing ospemifene in high yield and purity the method also being economically feasible and suitable for use in a large scale.

SUMMARY OF THE INVENTION

The present invention provides a process for the preparation of a compound of formula (I)

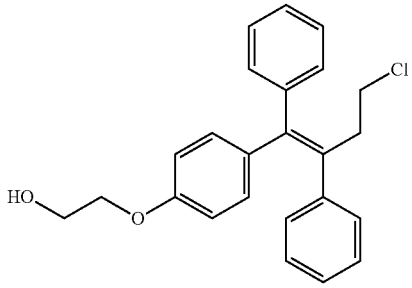

(I)

which process comprises
(a) reacting a compound of formula (III)

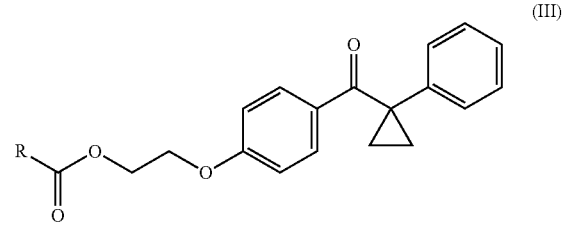

(III)

wherein R is a protecting group tolerant to Grignard or other organometallic reagents, with phenylmagnesium halide to produce a compound of formula (IV)

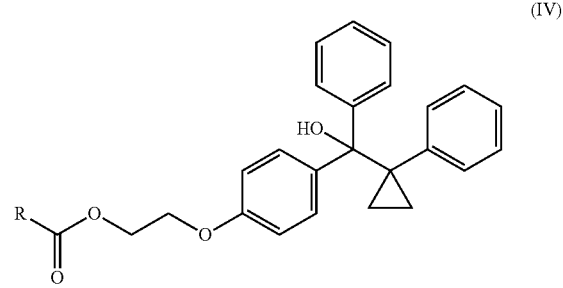

(IV)

wherein R is as defined above, and
(b) treating the compound of formula (IV) with hydrochloric acid to produce a compound of formula (V)

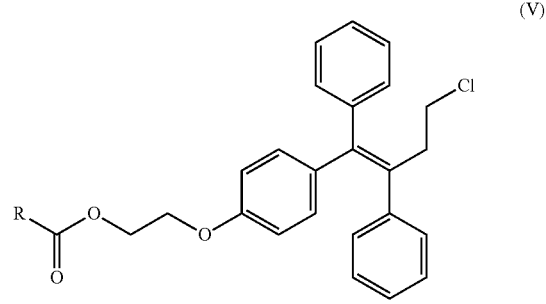

(V)

wherein R is as defined above, and
(c) cleaving the ester bond of a compound of formula (V) wherein R is as defined above, to give a compound of formula (I).

In another aspect, the present invention provides a process for the preparation of a compound of formula (I) comprising, the step of treating the compound of formula (IV), wherein R is a protecting group tolerant to Grignard or other organometallic reagents, with hydrochloric acid to produce a compound of formula (V), and cleaving the ester bond of a compound of formula (V) to give a compound of formula (I).

The invention is also directed to novel compounds of formula (III) and (IV) wherein R is t-butyl, adamantyl or 2,4,6-trimethylphenyl.

DETAILED DESCRIPTION OF THE INVENTION

The term "lower alcohol" means $C_{1-5}$ alcohol, preferably $C_{1-4}$ alcohol. Representative examples include methanol, ethanol, isopropanol and butanol, particularly preferred is methanol and ethanol.

In accordance with the present invention the compound of formula (III)

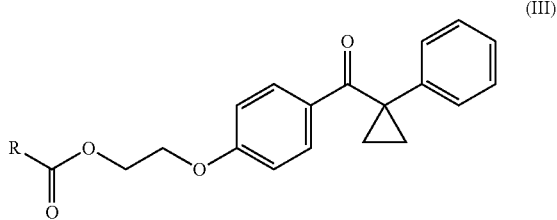

(III)

wherein R is a protecting group tolerant to Grignard or other organometallic reagents, is reacted with phenylmagnesium halide to produce a compound of formula (IV)

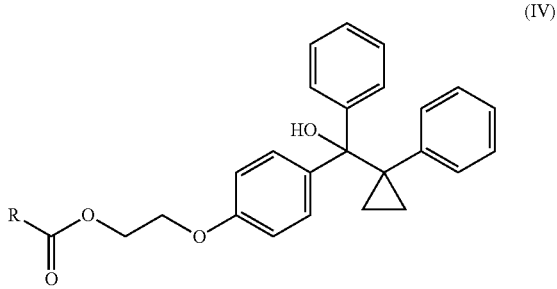

(IV)

wherein R is as defined above.

The above reaction is based on the nucleophilic addition of a phenylmagnesium halide (Grignard reagent), such as phenylmagnesium chloride or phenylmagnesium bromide, to the carbonyl group of the compound of formula (III). The reaction is carried out in suitable solvent, such as diethyl ether or THF, under nitrogen atmosphere. The reagents are suitably added at room temperature and the mixture is heated, for example to about 60° C. The reaction is typically completed within about 2-3 hours. The reaction can be quenched e.g. with addition of saturated $NH_4Cl$-solution. Phenylmagnesium halide reagent is at typically used in molar excess, e.g. in 1.5-2 molar equivalents per compound of formula (III). The resulting compound of formula (IV) can be isolated, if desired, by evaporation of the solvents and subsequent crystallization or the crude compound can be forwarded directly to the next step.

In the next step the compound of formula (IV) is subjected to dehydration and ring-opening reaction by treating it with hydrochloric acid to produce the ester compound of formula (V).

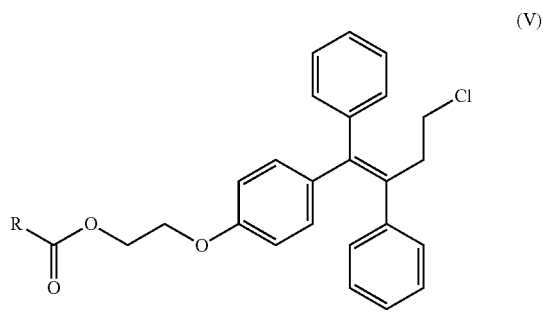

(V)

Thus, the compound of formula (IV) is dissolved in a suitable solvent such as dichloromethane (DCM) or toluene and this solution is added slowly to aqueous HCl solution, such as 30% HCl solution. The reaction is suitably carried out at room temperature. The reaction is typically completed within less than one hour.

The resulting ester of formula (V) is particularly suitable for being isolated and purified by crystallization before its use in the next reaction step. Thus, after completion of the ring opening reaction the reaction mixture can be poured on saturated $NaHCO_3$ solution and the organic phase is recovered. The organic phase is preferably evaporated and the crystallization solvent is added. Suitable crystallization solvents include plain lower alcohols, such as methanol and ethanol. Particularly suitable crystallization, solvents are methanol or ethanol essentially in the absence of water, thereby giving the ester of formula (V) in high yield and purity. The mixture of crystallization solvent and crude ester of formula (V) is stirred and suitably heated to achieve dissolution. The mixture may then be cooled to about 40° C. and seeded with the desired Z-isomer. Cooling is continued over a period of time (preferably slowly, e.g. over more than one hour) to room temperature or below, e.g. below 15° C., in order to achieve crystallization. The mixture is suitably stirred in this temperature for more than 3 hours, e.g. for 12 hours. The crystalline ester of formula (V) is filtered, washed and dried preferably under reduced pressure. The chemical purity of the crystallized compound of formula (V) is at this stage typically higher than 92% and the amount of E-isomer less than 5%. The end product may be further recrystallized if desired.

Compounds of formula (III) can be prepared using the methods known in the art.

For example, compound of formula (III) can be suitably prepared by reacting a compound of formula (II)

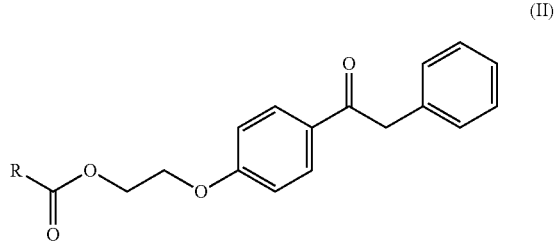

(II)

with a compound of formula $X_1—CH_2—CH_2—X_2$, wherein $X_1$ and $X_2$ is a leaving group and R is a protecting group tolerant to Grignard or other organometallic reagents. Suitable leaving groups $X_1$ and $X_2$ include, but are not limited to, halogens, para-toluenesulfonate ($CH_3C_6H_4SO_2O—$), methanesulfonate ($CH_3SO_2O—$) and trifluoromethanesulfonate ($CF_3SO_2O—$) groups. According to one embodiment of the invention $X_1$ and $X_2$ are halogens, in particular $X_1$ is Br and $X_2$ is Cl. The reaction between the compound of formula (II) and the compound of formula $X_1—CH_2—CH_2—X_2$ is suitably carried out in the presence of a phase transfer catalyst (PTC), such as quaternary ammonium or phosphonium salts. Examples of phase transfer catalyst include tetrabutylammonium hydrogensulfate (TBAHS), benzyltrimethylammonium chloride and hexadecyltributylphosphonium bromide. Thus, compound of formula (II) is dissolved in suitable solvent such as toluene under nitrogen atmosphere at room temperature followed by the addition of phase transfer catalyst such as TBAHS and aqueous NaOH solution (e.g. 50% NaOH solution) to the reaction mixture. The resulting two-phase system is stirred vigorously and the compound of formula $X_1—CH_2—CH_2—X_2$ is added dropwise. The reaction is typically completed within 12 hours. The organic phase is isolated, washed, filtered, dried and evaporated to obtain the compound of formula (III).

Alternatively, the reaction between the compound of formula (II) and the compound of formula $X_1—CH_2—CH_2—X_2$ can be carried out in an organic solvent, such as DMSO, DMF or THF, in the presence of a base such as NaH, K-, Na- or LiOBu-t, or corresponding carbonates.

Compounds of formula (II) can be prepared using the methods known in the art.

For example, compound of formula (II) can be suitably prepared by reacting a compound of formula (VI)

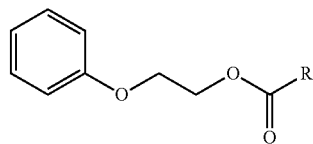

(VI)

wherein R is $C_{1-5}$ alkyl or an optionally substituted phenyl, with 2-phenylacetic acid. Typically, the reaction is catalyzed by a Brønsted acid, such as polyphosphoric acid (PPA). Thus, to warmed PPA is added compound of formula (VI) and 2-phenylacetic acid. After stirring for about 3 h, water is added and the mixture, is stirred further, at room temperature for about 2 h. The precipitated compound of formula (II) is filtered, washed and dried, and, if desired, recrystallised from suitable solvent, such as hexane/isopropanol (1:1).

According to one embodiment of the invention, particularly suitable compounds of formula (II), (III), (IV), (V) and (VI) are those wherein R is t-butyl, adamantyl or 2,4,6-trimethylphenyl. Particularly preferred compounds of formula (II), (III), (IV), (V) and (VI) are those wherein R is t-butyl.

The compound of formula (I) (ospemifene) is obtained by subjecting the compound of formula (V) to cleavage of the ester bond (dashed bond below) of the compound of formula (V)

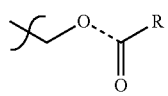

such that the hydroxyl group of ospemifene is formed.

The cleavage of the ester bond of the compound of formula (V) can be carried out by using well known methods such hydrolysis or a reductive cleavage.

Hydrolysis of the ester bond of the compound of formula (V) can be catalysed by a base or acid. A base catalysed hydrolysis is particularly preferred. The base catalysed hydrolysis can be carried in a suitable solvent such as aqueous THF or aqueous THF/MeOH mixture in the presence of a suitable base, such as NaOH or LiOH at room temperature for a time sufficient to complete the hydrolysis. When the hydrolysis is carried out at room temperature, the reaction is completed typically within 12 hours or less. Thereafter, water and suitable organic solvent such as EtOAc is added and the organic phase is washed, dried, filtered and concentrated. Ospemifene can be conveniently isolated from the residue by crystallization from a suitable crystallization solvent. Preferred solvents for crystallization are $C_{1-5}$ alcohols, particularly methanol, ethanol or isopropanol, or aqueous. $C_{1-5}$ alcohols such as aqueous methanol (e.g. 80% or 90% methanol).

Reductive cleavage of the ester bond of the compound of formula (V) to obtain ospemifene can be carried out in the presence of a reducing agent such as lithium aluminium hydride in a suitable organic solvent such as toluene, THF, hexane or xylene or mixture thereof. The reaction is suitably carried out at room temperature and under nitrogen atmosphere. The reaction may be suitably quenched by addition of saturated $NH_4Cl$-solution. Organic phase is washed, dried, filtered and concentrated. Ospemifene can be conveniently isolated from the residue by crystallization from a suitable crystallization solvent as described above:

The invention is further illustrated by the following non-limiting examples.

EXAMPLES

Example 1

Preparation of 2-phenoxyethyl pivalate

2-Phenoxyethanol (50 g, 0.362 mol) was dissolved in dichloromethane (500 ml) and the solution was cooled to 0-5° C. Triethylamine (101 ml, 0.724 mol) was added to the cooled solution followed by pivaloyl chloride (53.5 ml, 0.434 mol) maintaining the temperature, below 5° C. After additions the mixture was stirred at 5° C. for 30 min and at room temperature for 12 h. The reaction was quenched by addition of 1M HCl-solution (300 ml) and stirred vigorously. The phases were separated and organic phase was washed with saturated $NaHCO_3$-solution (2×150 ml), water (1×100 ml) and brine (1×100 ml). After drying ($Na_2SO_4$) and filtration the solvent was evaporated yielding the title compound (76.78 g, 0.345 mol, 95%) as a yellow oil. $^1$H-NMR (400 MHz, DMSO-$d_6$) δ (ppm): 7.31-7.27 (2H, m, ArH), 6.96-6.93 (3H, m, ArH), 4.34 (2H, m, $CH_2CH_2OPiv$), 4.19 (2H, m, $ArOCH_2CH_2$), 1.13 (9H, s, 3×Me). $^{13}$C-NMR (100 MHz, DMSO-$d_6$) δ (ppm): 177.7, 158.7, 130.1, 121.1, 114.9, 66.1, 62.9, 38.5, 27.6.

Example 2

Preparation of 2-(4-(2-Phenylacetyl)phenoxy)ethyl pivalate

Polyphosphoric acid (PPA) (250 g) was charged to a reaction vessel and warmed to 50° C. (bath temperature) with mechanical stirring. 2-Phenylacetic acid (30.6 g, 0.225 mol) was added to PPA followed by 2-phenoxyethyl pivalate (50 g, 0.225 mol). After 3 hours TLC and HPLC indicated full conversion and water (1000 ml) was added. The mixture was stirred at room temperature for 2 h. The precipitated product was filtered and washed with water (300 ml). After drying in vacuo the crude product (65 g) was re-crystallized with hexane/i-PrOH 1:1 yielding the title compound as slightly yellow solid (51.49 g, 0.151 mol, 67%). $^1$H-NMR (400 MHz, DMSO-$d_6$) δ (ppm): 8.02 (2H, d, J=9.2 Hz, ArH), 7.32-7.22 (5H, m, ArH), 7.07 (2H, d, J=8.8 Hz, ArH), 4.37 (2H, m, $CH_2CH_2OPiv$), 4.31 (2H, s, $ArCH_2CO$), 4.3 (2H, m, $ArOCH_2CH_2$), 1.12 (9H, s, 3×Me). $^{13}$C-NMR (100 MHz, DMSO-$d_6$) δ (ppm): 196.4, 177.7, 162.6, 135.8, 131.2, 129.9, 129.8, 128.7, 126.8, 114.8, 66.5, 62.7, 44.8, 38.6, 27.2.

Example 3

Preparation of 2-(4-(1-Phenylcyclopropanecarbonyl)phenoxy ethyl pivalate 2-(4-(2-Phenylacetyl)phenoxy)ethyl pivalate (15 g, 44.1 mmol) was dissolved in nitrogen bubbled toluene (150 ml) and stirred under nitrogen atmosphere for 10 min at room temperature. Tetrabutylammonium hydrogensulfate (1.496 g, 4.41 mmol) catalyst was added to the stirred solution followed by 50% NaOH-solution (60 ml, 1137 mmol). The two-phase system was stirred vigorously for 10 min. 1-Bromo-2-chloroethane (9.17 mL, 110 mmol) was dissolved in toluene (35 ml) and added dropwise to the stirred reaction mixture. After 12 hours the starting material was consumed and water (100 ml) was added. The phases were separated and the aqueous layer was extracted with toluene (50 ml). The combined toluene phases were washed with water (100 ml) and brine (100 ml). After drying ($Na_2SO_4$) and filtration toluene was removed in vacuo. Crude title compound (15.39 g, 42 mmol, 95%) was obtained as sticky brown oil contained with 15% of O-alkylated by-product. $^1$H-NMR (400 MHz, $CDCl_3$) δ (ppm): 7.80 (2H, d, J=9.2 Hz, ArH), 7.26-7.16 (5H, m, ArH), 6.77 (2H, d, J=8.8 Hz, ArH), 4.37 (2H, t, J=4.8 Hz, $CH_2CH_2OPiv$), 4.15 (2H, t, J=5.0 Hz, $ArOCH_2CH_2$), 1.60 (2H, AB-system, J=4.4 Hz, $CH_2CH_2$), 1.32 (2H, AB-system, J=4.4 Hz, $CH_2CH_2$), 1.17 (9H, s, 3×Me). $^{13}$C-NMR (100 MHz, $CDCl_3$) δ (ppm): 198.6, 178.9, 162.1, 141.7, 132.3, 130.2, 129.1, 127.9, 126.8, 114.2, 67.0, 62.8, 39.2, 35.0, 27.5, 16.1.

Example 4

Preparation of (Z)-2-(4-(4-Chloro-1,2-diphenylbut-1-en-1-yl)-phenoxy)ethyl pivalate Crude 2-(4-(1-Phenylcyclopropanecarbonyl)phenoxy) ethyl pivalate (15.3 g, 41.8 mmol) was dissolved in tetrahydrauran (THF) (200 ml) under nitrogen with stirring. 1 M THF-solution of phenylmagnesium chloride (35.5 ml, 71 mmol) was added dropwise to the solution at room temperature. After addition the reaction was warmed to 60° C. and kept at this temperature for two hours. The reaction was quenched by addition of saturated $NH_4Cl$-solution (300 ml). The pH was adjusted to 4 with 5% HCl-solution and THF-phase was separated. The aqueous phase was extracted with dichloromethane (2×75 ml), combined with THF-phase, and washed with water (100 ml) and brine (100 ml). After drying ($Na_2SO_4$) and filtration the solvents were evaporated and crude cyclopropylcarbinol intermediate (21 g) was directly submitted to the ring-opening step. The crude cyclopropylcarbinol intermediate was dissolved in dichloromethane (DCM) (150 ml) and treated with 30% HCl-solution (120 ml). After 60 min the dehydration and ring-opening was complete and reaction mixture was poured on saturated $NaHCO_3$-solution (350 ml). The phases were separated and DCM-phase was washed with water (100 ml) and brine (100 ml). After drying ($Na_2SO_4$) and filtration the solvent was evaporated. The residue was dissolved in boiling methanol, cooled to 40° C. and seeded. After stirring at room temperature (12 h) the precipitated title compound was filtered and washed with cold MeOH. The title compound was obtained as a white solid (5.4 g, 11.7 mmol, 28% over two steps). $^1$H-NMR (400 MHz, $CDCl_3$) δ (ppm): 7.39-7.13 (6H, m, ArH), 6.79 (2H, d, J=8.8 Hz, ArH), 6.56 (2H, d, J=8.8 Hz, ArH), 4.31 (2H, t, J=4.4 Hz, $CH_2CH_2OPiv$), 4.04 (2H, t, J=4.8 Hz, $ArOCH_2CH_2$), 3.41 (2H, t, J=7.6 Hz, $ClCH_2CH_2$), 2.92 (2H, t, 1=7 0.6 Hz, $ClCH_2CH_2$), 1.17 (9H, s, 3×Me). $^{13}$C-NMR (100 MHz, $CDCl_3$) δ (ppm): 178.5, 156.8, 142.8, 141.6, 140.9, 135.3, 135.2, 131.7, 129.5, 129.4, 128.4, 128.2, 127.0, 126.6, 113.6, 65.7, 62.7, 42.8, 38.7, 38.6, 27.1.

Example 5

Preparation of (Z)-2-[4-(4-chloro-1,2-diphenyl-but-1-enyl)-phenoxy]ethanol (ospemifene) by Base Hydrolysis of Pivaloyl-Group (Z)-2-(4-(4-Chloro-1,2-diphenylbut-1-en-1-yl)phenoxy) ethyl pivalate (1 g, 2.16 mmol) was dissolved in THF (8 ml) followed by addition of MeOH (1 ml) and water (1 ml). Sodium hydroxide (0.1 g, 2.5 mmol) was added in one portion and the reaction was stirred at room temperature for 12 h. After completion of the reaction the mixture was partitioned between water (20 ml) and EtOAc (20 ml). Organic phase was washed with water (20 ml) and brine (20 ml), dried ($Na_2SO_4$), filtered and concentrated. The residue was crystallized from i-PrOH yielding ospemifene (0.29 g, 35%) as a white solid. $^1$H-NMR (400 MHz, $CDCl_3$) δ (ppm): 7.37 (2H, t, J=8 Hz, ArH), 7.29 (3H, t, J=7.2 Hz, ArH), 7.20 (2H, t, J=7.6 Hz, ArH), 7.16-7.13 (3H, m, ArH), 6.80 (2H, d, J=8.8 Hz, ArH), 6.57 (2H, d, J=8.8 Hz, ArH), 3.94 (2H, t, J=4.4 Hz, $ArOCH_2CH_2OH$), 3.87 (2H, m, $ArOCH_2CH_2OH$), 3.42 (2H, t, J=7.2 Hz, $ClCH_2CH_2$), 2.92 (2H, t, J=7.2 Hz, $ClCH_2CH_2$), 1.95 (1H, t, J=6.4 Hz, OH). $^{13}$C-NMR (100 MHz, $CDCl_3$) δ (ppm): 157.2, 143.2, 142.1, 141.3, 2×135.7, 132.2, 130.0, 129.8, 128.8, 128.7, 127.4, 127.0, 113.9, 69.3, 61.8, 43.3, 39.0.

Example 6

Preparation of (Z)-2-[4-(4-chloro-1,2-diphenyl-but-1-enyl)-phenoxy]ethanol (Ospemifene) by Reductive Cleavage of Pivaloyl-Group (Z)-2-(4-(4-Chloro-1,2-diphenylbut-1-en-1-yl)phenoxy) ethyl pivalate (3.5 g, 7.56 mmol) was dissolved in toluene (35 ml) and stirred under nitrogen for 5 min at room temperature.

Lithium aluminium hydride solution (1 M in THF) (7.56 ml, 7.56 mmol) was added dropwise to the reaction and the mixture was stirred at room temperature for 30 min. After HPLC indicated completion, the reaction was quenched by addition of saturated $NH_4Cl$-solution (75 ml). Additional amount of toluene (30 ml) was added and the phases were separated. The organic phase was washed with water (50 ml), brine (50 ml), dried ($Na_2SO_4$), filtered and concentrated in vacuo. The residue was crystallized froth 90% MeOH yielding ospemifene (1.75 g, 61%) as a white solid.

The invention claimed is:

1. A process of preparing a compound of formula (I)

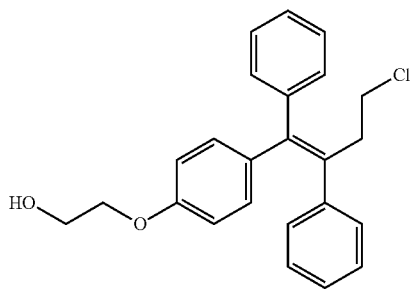

(I)

which process comprises (a) reacting a compound of formula (III)

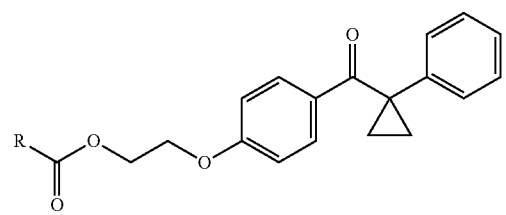

(III)

wherein R is a protecting group tolerant to Grignard or other organometallic reagents, with phenylmagnesium halide, thereby obtaining a compound of formula (IV)

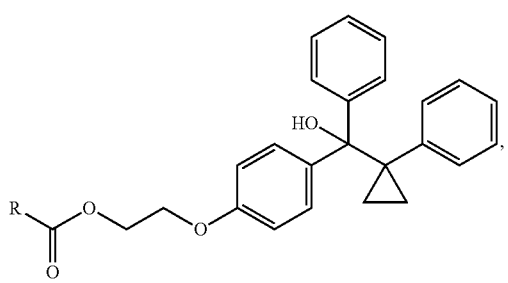

(IV)

wherein R is as defined in formula (III), (b) treating the compound of formula (IV) with hydrochloric acid, thereby obtaining a compound of formula (V)

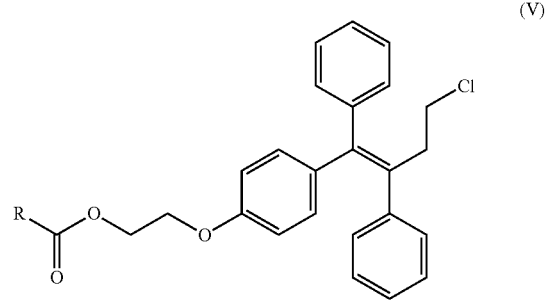

(V)

wherein R is as defined as in formula (III), and (c) cleaving the ester bond of the compound of formula (V), thereby obtaining the compound of formula (I).

2. The process according to claim 1, wherein the phenylmagnesium halide is phenylmagnesium chloride.

3. The process according to claim 1, further comprising isolating the compound of formula (V) by crystallization.

4. The process according to claim 3, wherein the crystallization of the compound of formula (V) is from a lower alcohol.

5. The process according to claim 4, wherein the lower alcohol is methanol or ethanol.

6. The process according to claim 1, wherein (c) cleaving the ester bond of the compound of formula (V) is carried out by a base catalyzed hydrolysis or a reductive cleavage.

7. The process according to claim 6, wherein (c) cleaving the ester bond comprises reductive cleavage in the presence of lithium aluminum hydride.

8. The process according to claim 1, further comprising isolating the compound of formula (I) by crystallization.

9. The process according to claim 8, wherein isolating the compound of formula (I) comprises crystallizing the compound of formula (I) from $C_{1-5}$ alcohol or from a mixture of $C_{1-5}$ alcohol and water.

10. The process according to claim 1, wherein R is t-butyl, adamantyl or 2,4,6-trimethylphenyl.

11. The process according to claim 10, wherein R is t-butyl.

12. The process according to claim 1, further comprising preparing the compound of formula (III) by reacting a compound of formula (II)

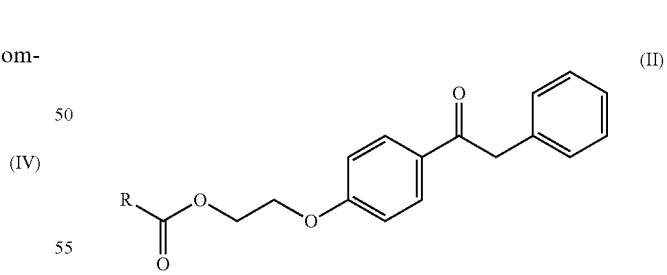

(II)

with a compound of formula $X_1$—$CH_2$—$CH_2$—$X_2$, wherein $X_1$ and $X_2$ are each a leaving group and R is a protecting group tolerant to Grignard or other organometallic reagents.

13. The process according to claim 12, wherein $X_1$ is halogen and $X_2$ is halogen.

14. The process according to claim 13, wherein $X_1$ is Br and $X_2$ is Cl.

15. The process according to claim 12, wherein R is t-butyl, adamantyl or 2,4,6-trimethylphenyl.

16. The process according to claim 15, wherein R is t-butyl.

17. The process according to claim 12, wherein reacting the compound of formula (II) with the compound of formula $X_1$—CH,—CH,—$X_2$ is carried out in the presence of a phase transfer catalyst.

18. The process according to claim 17, wherein the phase transfer catalyst is tetrabutylammonium hydrogensulfate (TBAHS).

19. The process according to claim 12, further comprising preparing the compound of formula (II) by reacting a compound of formula (VI)

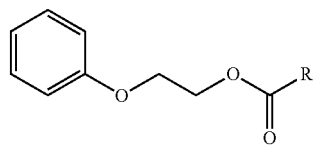

wherein R is a protecting group tolerant to Grignard or other organometallic reagents,
with 2-phenylacetic acid.

20. The process according to claim 19, wherein R is t-butyl, adamantyl or 2,4,6-trimethylphenyl.

21. The process according to claim 20, wherein R is t-butyl.

22. A process of preparing a compound of formula (I)

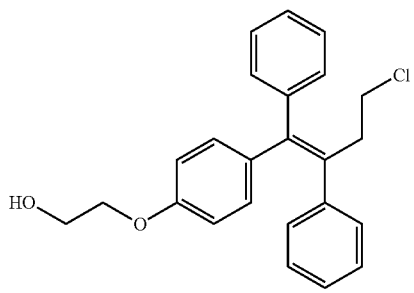

the process comprising treating a compound of formula (IV)

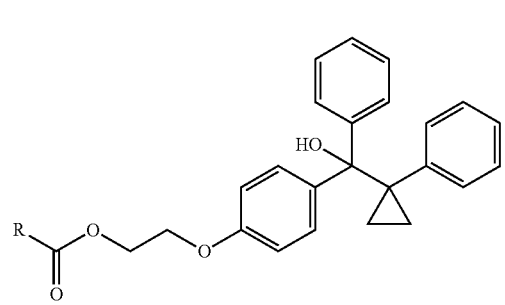

wherein R is a protecting group tolerant to Grignard or other organometallic reagents,
with hydrochloric acid, thereby obtaining a compound of formula (V)

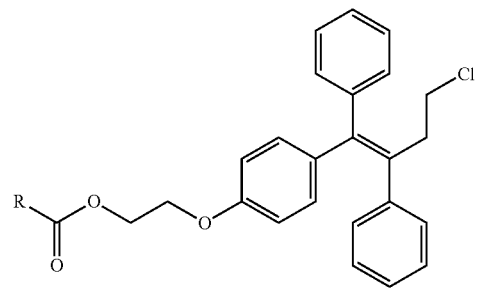

wherein R is as in formula (IV), and
cleaving the ester bond of the compound of formula (V), thereby obtaining the compound of formula (I).

23. The process according to claim 2, wherein R is t-butyl, adamantyl or 2,4,6-trimethylphenyl.

24. The process according to claim 23, wherein R is t-butyl.

25. A compound of formula (III)

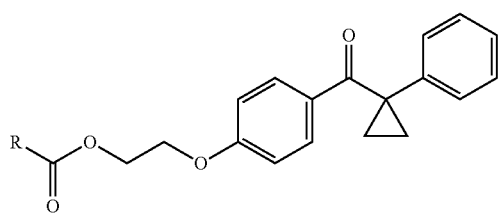

wherein R is t-butyl, adamantyL or 2,4,6-trimethylphenyl.

26. The compound according to claim 25, wherein R is t-butyl.

27. A compound of formula (IV)

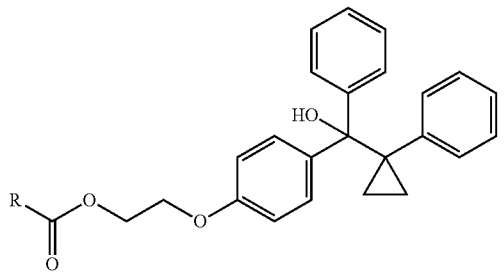

wherein R is t-butyl, adamantyl or 2,4,6-trimethylphenyl.

28. The compound according to claim 27, wherein R is t-butyl.

29. The process of claim 3, wherein a chemical purity of the compound of formula (V) immediately after the crystallization is higher than 92%.

30. The process of claim 3, wherein the compound of formula (V) immediately after the crystallization has a content of less than 5% of an E-isomer of the compound of formula (V).

* * * * *